(12) United States Patent
Nakamura

(10) Patent No.: US 12,282,730 B2
(45) Date of Patent: Apr. 22, 2025

(54) DOCUMENT CREATION SUPPORT APPARATUS, DOCUMENT CREATION SUPPORT METHOD, AND PROGRAM

(71) Applicant: FUJIFILM Corporation, Tokyo (JP)

(72) Inventor: Keigo Nakamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 151 days.

(21) Appl. No.: 17/878,038

(22) Filed: Jul. 31, 2022

(65) Prior Publication Data
US 2022/0382967 A1 Dec. 1, 2022

Related U.S. Application Data

(63) Continuation of application No. PCT/JP2021/004410, filed on Feb. 5, 2021.

(30) Foreign Application Priority Data

Feb. 7, 2020 (JP) .................................. 2020-020144
Dec. 22, 2020 (JP) .................................. 2020-212842

(51) Int. Cl.
*G06F 17/00* (2019.01)
*G06F 40/166* (2020.01)
(Continued)

(52) U.S. Cl.
CPC .......... *G06F 40/166* (2020.01); *G06T 7/0012* (2013.01); *G06V 10/764* (2022.01);
(Continued)

(58) Field of Classification Search
CPC ........ G06F 40/166; G06F 40/44; G06F 40/56;
G16H 70/60; G16H 15/00; G16H 30/20;
G16H 30/40; G16H 40/67; G16H 50/20;
G16H 50/70; G06V 20/70; G06V 10/764;
G06V 2201/03; G06T 7/0012; G06T
2207/10072; G06T 2207/10116;
(Continued)

(56) References Cited

U.S. PATENT DOCUMENTS 5,807,256 A 9/1998 Taguchi et al.
6,785,410 B2 * 8/2004 Vining .................. G06Q 10/10
382/128
(Continued)

FOREIGN PATENT DOCUMENTS

CN 108491497 A * 9/2018 ............. G06F 40/00
JP S62197864 9/1987
(Continued)

OTHER PUBLICATIONS

"International Search Report (Form PCT/ISA/210) of PCT/JP2021/004410," mailed on Apr. 20, 2021, with English translation thereof, pp. 1-5.
(Continued)

*Primary Examiner* — Laurie A Ries
(74) *Attorney, Agent, or Firm* — JCIPRNET

(57) ABSTRACT

A text generation unit (14) generates a plurality of texts which describe properties of feature portions and are different from each other for at least one feature portion included in an image. A display control unit (15) performs control such that each of the plurality of texts is displayed on a display unit.

20 Claims, 13 Drawing Sheets

(51) Int. Cl.
  *G06T 7/00* (2017.01)
  *G06V 10/764* (2022.01)
  *G06V 20/70* (2022.01)
  *G16H 70/60* (2018.01)

(52) U.S. Cl.
  CPC ............ *G06V 20/70* (2022.01); *G16H 70/60* (2018.01); *G06V 2201/03* (2022.01)

(58) Field of Classification Search
  CPC . G06T 2207/20084; G06T 2207/30061; G06T 2207/30096; G06T 1/00
  USPC ......................................... 715/256
  See application file for complete search history.

(56) References Cited

U.S. PATENT DOCUMENTS

| | | | |
|---|---|---|---|
| 7,894,676 B2* | 2/2011 | Iizuka | G16H 15/00 382/209 |
| 8,593,436 B2* | 11/2013 | Anwar | G06F 3/04883 345/173 |
| 10,453,456 B2* | 10/2019 | Nicholls | G10L 15/1822 |
| 10,733,372 B2* | 8/2020 | Kumar | G06F 40/186 |
| 10,769,782 B2* | 9/2020 | Popp | G06T 7/0012 |
| 11,141,115 B2* | 10/2021 | Benson | G16H 20/40 |
| 11,978,274 B2* | 5/2024 | Ichinose | G06V 30/19007 |
| 2010/0189366 A1 | 7/2010 | Iizuka et al. | |
| 2019/0279751 A1 | 9/2019 | Nakamura et al. | |
| 2021/0090748 A1* | 3/2021 | Toyoshiba | G16H 10/60 |
| 2021/0166807 A1* | 6/2021 | Quennesson | G06T 7/0012 |

FOREIGN PATENT DOCUMENTS

| | | |
|---|---|---|
| JP | 10731591 | 2/1995 |
| JP | 2009082443 | 4/2009 |
| JP | 2009259000 | 11/2009 |
| JP | 2019153250 | 9/2019 |

OTHER PUBLICATIONS

"Written Opinion of the International Searching Authority (Form PCT/ISA/237)" of PCT/JP2021/004410, mailed on Apr. 20, 2021, with English translation thereof, pp. 1-8.

"Office Action of Japan Counterpart Application", issued on May 9, 2023, with English translation thereof, p. 1-p. 12.

* cited by examiner

FIG. 7

```
START
  ↓
ACQUIRE DIAGNOSIS TARGET IMAGE — ST1
  ↓
EXTRACT ABNORMAL SHADOW — ST2
  ↓
ANALYZE ABNORMAL SHADOW — ST3
  ↓
GENERATE TEXT — ST4
  ↓
PERFORM DISPLAY CONTROL — ST5
  ↓
END
```

FIG. 8

| PROPERTY ITEM | PROPERTY | PROPERTY SCORE |
|---|---|---|
| POSITION | LEFT UPPER LOBE | 1.00 |
| PRESENCE OR ABSENCE OF PLEURAL INVAGINATION | PLEURAL INVAGINATION + | 0.98 |
| PRESENCE OR ABSENCE OF IRREGULAR MARGIN | IRREGULAR MARGIN + | 0.62 |
| PRESENCE OR ABSENCE OF SPICULA | SPICULA + | 0.56 |
| SIZE | 4.2 cm | 0.81 |
| TYPE OF DISEASE | TUMOR | 0.92 |

FIG. 10

| NODULE IS FOUND. | ~T1 |

| HEMANGIOMA IS FOUND. | ~T2 |

| CYST IS FOUND. | ~T3 |

FIG. 11

SOLID TUMOR WITH MAJOR AXIS OF 2.1 cm IS FOUND IN LEFT UPPER LOBE.
PRIMARY LUNG CANCER IS SUSPECTED ~T1

SOLID TUMOR WITH MAJOR AXIS OF 2.1 cm IS FOUND IN LEFT UPPER LOBE.
THERE IS HIGH LIKELIHOOD OF BENIGNITY ~T2

FIG. 12

SOLID TUMOR WITH MAJOR AXIS OF 2.1 cm IS FOUND IN LEFT UPPER LOBE.
IT IS PRIMARY LUNG CANCER. ~T1

SOLID TUMOR WITH MAJOR AXIS OF 2.1 cm IS FOUND IN LEFT UPPER LOBE.
PRIMARY LUNG CANCER IS SUSPECTED. ~T2

SOLID TUMOR WITH MAJOR AXIS OF 2.1 cm IS FOUND IN LEFT UPPER LOBE.
LIKELIHOOD OF PRIMARY LUNG CANCER CANNOT BE DENIED. ~T3

| CLASSIFICATION OF DISEASE | FIRST RELEVANT PORTION | DETERMINATION ITEM FOR FIRST RELEVANT PORTION | SECOND RELEVANT PORTION | DETERMINATION ITEM FOR SECOND RELEVANT PORTION |
|---|---|---|---|---|
| LUNG NODULE | AREA BETWEEN VISCERAL PLEURA AND PARIETAL PLEURA | PRESENCE OR ABSENCE OF PLEURAL EFFUSION | LYMPH NODE | PRESENCE OR ABSENCE OF LYMPHADENOPATHY |
| ATELECTASIS | - | - | - | - |
| ⋮ | ⋮ | ⋮ | ⋮ | ⋮ |

FIG. 15

| SOLID NODULE WITH MAJOR AXIS OF 2.1 cm IS FOUND IN LEFT UPPER LOBE. NO PLEURAL EFFUSION IS FOUND. | ~T1 |

| SOLID NODULE WITH MAJOR AXIS OF 2.1 cm IS FOUND IN LEFT UPPER LOBE. NO LYMPHADENOPATHY IS FOUND. | ~T2 |

| SOLID NODULE WITH MAJOR AXIS OF 2.1 cm IS FOUND IN LEFT UPPER LOBE. NO PLEURAL EFFUSION IS FOUND. NO LYMPHADENOPATHY IS FOUND. | ~T3 |

FIG. 17

| SOLID NODULE WITH MAJOR AXIS OF 2.1 cm IS FOUND IN LEFT UPPER LOBE. NO PLEURAL EFFUSION IS FOUND. NO LYMPHADENOPATHY IS FOUND. | ~T1 |

| ATELECTASIS WITH MAJOR AXIS OF 2.1 cm IS FOUND IN LEFT UPPER LOBE. | ~T2 |

FIG. 18

| SOLID NODULE WITH MAJOR AXIS OF 2.1 cm IS FOUND IN LEFT UPPER LOBE. PRIMARY LUNG CANCER IS SUSPECTED. NO PLEURAL EFFUSION IS FOUND. NO LYMPHADENOPATHY IS FOUND. | ~T1 |

| SOLID NODULE WITH MAJOR AXIS OF 2.1 cm IS FOUND IN LEFT UPPER LOBE. THERE IS HIGH LIKELIHOOD OF BENIGNITY. | ~T2 |

DOCUMENT CREATION SUPPORT APPARATUS, DOCUMENT CREATION SUPPORT METHOD, AND PROGRAM

CROSS-REFERENCE TO RELATED APPLICATION

This application is a continuation application of International Application No. PCT/JP2021/004410, filed Feb. 5, 2021, the disclosure of which is incorporated herein by reference in its entirety. Further, this application claims priority from Japanese Patent Application No. 2020-020144 filed on Feb. 7, 2020 and Japanese Patent Application No. 2020-212842 filed on Dec. 22, 2020, the disclosures of which is incorporated herein by reference in its entirety.

BACKGROUND

1. Technical Field

Disclosed technologies relate to a document creation support apparatus, a document creation support method, and a program.

2. Description of the Related Art

The following technologies are known as technologies related to a document creation support apparatus that creates texts that can be applied to documents such as interpretation reports based on medical images. For example, JP2019-153250A describes a medical document creation support apparatus comprising an input reception unit, an analysis result acquisition unit, and a document creation unit, the input reception unit being configured to receive input of a keyword representing a finding based on a displayed medical image, the analysis result acquisition unit being configured to acquire an analysis result of the medical image, and the document creation unit being configured to create a medical document related to the medical image based on the keyword and on the analysis result.

Further, JP2009-259000A describes a document creation support apparatus comprising an operation input control unit, a registration unit, a search unit, and a display control unit, the operation input control unit being configured to select a desired term from a plurality of terms prepared in advance, select terms to be used as a sentence from a fixed phrase generated according to a combination of selected terms or input candidates, receive corrections to the selected sentence, and use the corrected sentence as a correction sentence, the registration unit being configured to associate a combination of terms selected by the operation input control unit with the correction sentence and to register it in a dictionary, the search unit being configured to search the dictionary for a correction sentence in which the combination of terms selected by the operation input control unit and a combination of terms associated with the registration unit match, and the display control unit being configured to display the correction sentence found by the search unit as an input candidate for the sentence selected by the operation input control unit.

SUMMARY

A text that is automatically generated based on the medical image may be missing important information or may contain non-important information, and thus a text having content that matches a user's request may not always be generated. In order to deal with this, it is conceivable to present a plurality of candidate texts having different descriptions and to allow the user to select a text that matches the user's request from among the plurality of candidate texts. In this case, it is preferable that the plurality of candidate texts have a variety of description contents or expressions. As a result, there is a high likelihood that texts that match the user's request are included in the plurality of candidate texts.

The disclosed technology has been made in view of the above points, and an object thereof is to generate a plurality of texts having a variety of description contents or expressions in a case of automatically generating texts based on images.

According to an aspect of the disclosed technology, there is provided a document creation support apparatus comprising at least one processor. The processor is configured to generate a plurality of texts including different descriptions for at least one feature portion included in an image, and perform control such that each of the plurality of texts is displayed on a display unit.

The processor may be configured to generate the plurality of texts which describe properties of the feature portion and are different from each other.

The processor may be configured to specify the properties of the feature portion for each of a plurality of predetermined property items, and generate the plurality of texts such that at least one of the specified properties is described in each of the plurality of texts and a combination of property items corresponding to the properties described in each of the plurality of texts is different between the plurality of texts.

The processor may be configured to derive a property score indicating a prominence of the property for each of the plurality of property items, and determine the combination based on the property score.

The processor may be configured to generate the plurality of texts such that each text includes a description of the same content with different expressions between the plurality of texts. In this case, the processor may be configured to generate the plurality of texts such that a description of a designated property among a plurality of properties specified for the feature portion has the same content with different expressions between the plurality of texts.

The processor may be configured to generate the plurality of texts which describe a classification of a disease corresponding to the feature portion and are different from each other. The processor may be configured to generate the plurality of texts such that the classification of the disease described in each of the plurality of texts is different between the plurality of texts. The processor may be configured to estimate the classification of the disease corresponding to the feature portion, and perform control such that the plurality of texts are arranged in order according to an estimation result of the classification of the disease and are displayed on the display unit. The processor may be configured to generate the plurality of texts such that both a text indicating that the disease is benign and a text indicating that the disease is malignant are included. The processor may be configured to generate the plurality of texts such that, in the description regarding the classification of the disease, an expression indicating a probability that the disease corresponds to the classification is different between the plurality of texts.

The processor may include, in at least one of the plurality of texts, a description regarding a relevant portion related to the classification of the disease described in each of the plurality of texts for the feature portion. The processor may be configured to generate the plurality of texts such that the number or combination of the relevant portions described in the plurality of texts is different between the plurality of texts. The processor may include the description regarding the relevant portion only in a text, among the plurality of texts, in which the classification of the disease described for the feature portion is a specific classification. The processor may include the description regarding the relevant portion only in a text, among the plurality of texts, in which the classification of the disease described for the feature portion is malignant. The processor may be configured to receive a designation of the feature portion, and perform control such that a plurality of texts related to the designated feature portion among a plurality of texts generated in advance are displayed on the display unit. The processor may be configured to generate the plurality of texts such that a description regarding a size of the feature portion is different between the plurality of texts. The processor may be configured to generate the plurality of texts such that a description regarding the number, an amount, a density, or a distribution state of the feature portions is different between the plurality of texts.

According to another aspect of the disclosed technology, there is provided a document creation support method comprising: generating a plurality of texts which describe properties of feature portions and are different from each other for at least one feature portion included in an image; and displaying each of the plurality of texts on a display unit.

According to another aspect of the disclosed technology, there is provided a program for causing a computer to execute a process comprising: generating a plurality of texts which describe properties of feature portions and are different from each other for at least one feature portion included in an image; and displaying each of the plurality of texts on a display unit.

According to the disclosed technology, it is possible to create a plurality of texts having a variety of description contents or expressions in a case of automatically generating texts based on images.

BRIEF DESCRIPTION OF THE DRAWINGS

Exemplary embodiments according to the technique of the present disclosure will be described in detail based on the following figures, wherein:

FIG. 7 is a flowchart showing an example of a flow of a document creation support process according to an embodiment of the disclosed technology;

FIG. 8 is a diagram showing an example of a property score according to an embodiment of the disclosed technology;

FIG. 10 is a diagram showing an example of a plurality of texts generated by the text generation unit according to an embodiment of the disclosed technology;

FIG. 11 is a diagram showing an example of a plurality of texts generated by the text generation unit according to an embodiment of the disclosed technology;

FIG. 12 is a diagram showing an example of a plurality of texts generated by the text generation unit according to an embodiment of the disclosed technology;

FIG. 15 is a diagram showing an example of a plurality of texts generated by the text generation unit according to an embodiment of the disclosed technology;

FIG. 17 is a diagram showing an example of a plurality of texts generated by the text generation unit according to an embodiment of the disclosed technology;

FIG. 18 is a diagram showing an example of a plurality of texts generated by the text generation unit according to an embodiment of the disclosed technology.

DETAILED DESCRIPTION

Figure 1:
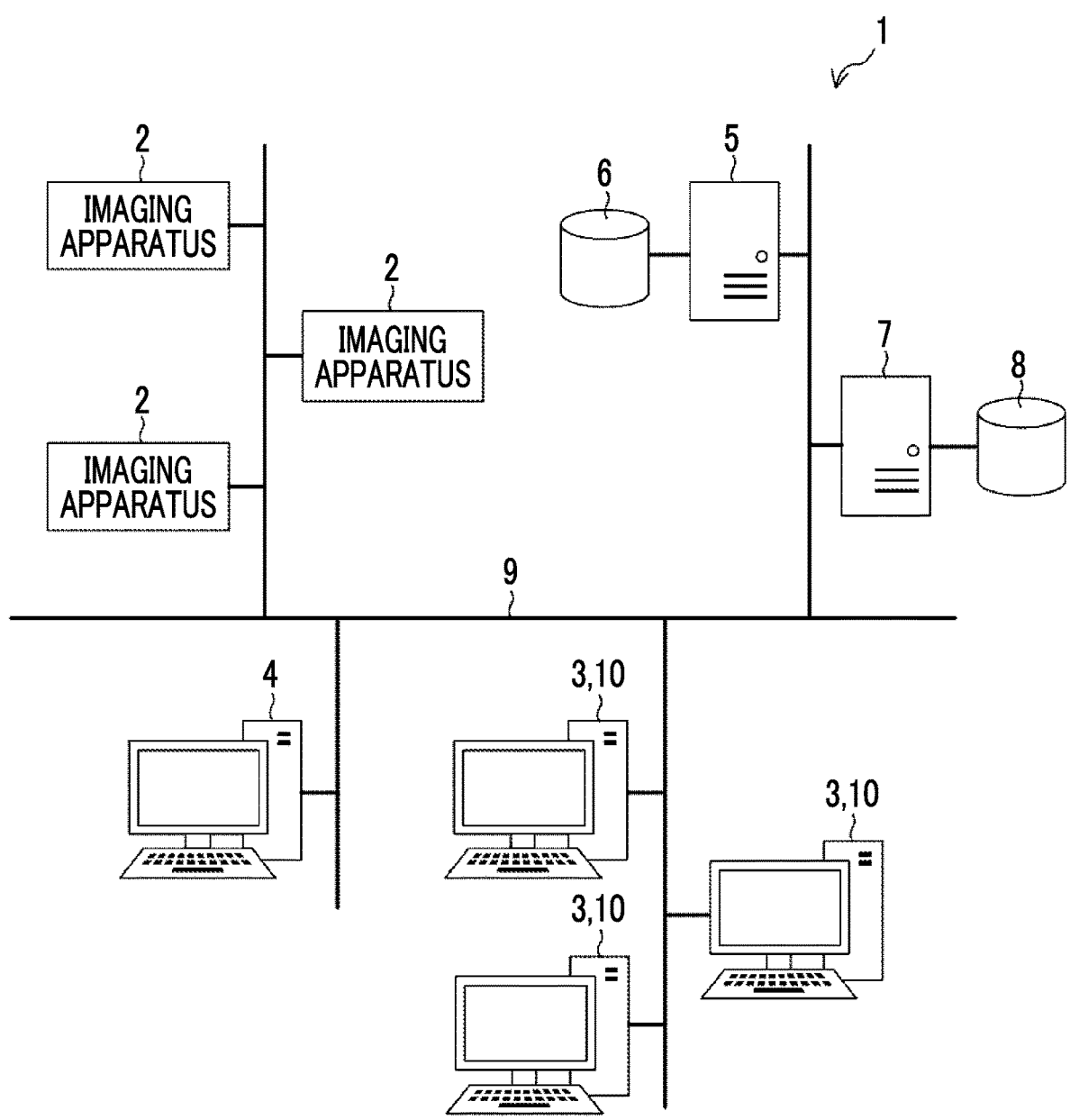
FIG. 1 is a diagram showing a schematic configuration of a medical information system according to an embodiment of the disclosed technology.

Hereinafter, embodiments of the disclosed technology will be described with reference to the drawings. In each drawing, substantially the same or equivalent components or portions are designated by the same reference numerals.

First Embodiment

FIG. 1 is a diagram showing a schematic configuration of a medical information system 1 to which a document creation support apparatus according to an embodiment of the disclosed technology is applied. The medical information system 1 is, based on an examination order from a doctor in a medical department using a known ordering system, a system for imaging an examination target part of a subject, storing a medical image acquired by the imaging, interpreting the medical image by a radiologist and creating an interpretation report, and viewing the interpretation report and observing the medical image to be interpreted in detail by the doctor in the medical department that is a request source.

In the medical information system 1, a plurality of imaging apparatuses 2, a plurality of interpretation workstations (WS) 3 that are interpretation terminals, a medical department workstation (WS) 4, an image server 5, an image database 6, an interpretation report server 7, and an interpretation report database 8 are communicably connected to each other through a wired or wireless network 9.

Each apparatus is a computer on which an application program for causing each apparatus to function as a component of the medical information system 1 is installed. The application program is recorded on a recording medium, such as a digital versatile disc (DVD) or a compact disc read only memory (CD-ROM), and distributed, and is installed on the computer from the recording medium. Alternatively, the application program is stored in a storage apparatus of a server computer connected to the network 9 or in a network storage in a state in which it can be accessed from the outside, and is downloaded to and installed on the computer in response to a request.

The imaging apparatus 2 is an apparatus that generates a medical image showing a diagnosis target part of the subject by imaging the diagnosis target part. The imaging apparatus 2 may be, for example, a simple X-ray imaging apparatus, a CT apparatus, an MRI apparatus, a positron emission tomography (PET) apparatus, and the like. A medical image generated by the imaging apparatus 2 is transmitted to the image server 5 and is saved therein.

The medical department WS 4 is a computer used by a doctor in a medical department to observe a medical image in detail, view an interpretation report, create an electronic medical record, and the like, and includes a processing apparatus, a display apparatus such as a display, and an input apparatus such as a keyboard and a mouse. In the medical department WS 4, each process such as creating a medical record (electronic medical record) of a patient, requesting to view an image from the image server 5, displaying a medical image received from the image server 5, automatically detecting or highlighting suspected disease regions in the medical image, requesting to view an interpretation report from the interpretation report server 7, and displaying the interpretation report received from the interpretation report server 7 is performed by executing a software program for each process.

The image server 5 is a general-purpose computer on which a software program that provides a function of a database management system (DBMS) is installed. The image server 5 comprises the image database 6 including a storage. The image database 6 may be a hard disk apparatus connected to the image server 5 by a data bus, or may be a disk apparatus connected to a storage area network (SAN) or a network attached storage (NAS) connected to the network 9. In a case where the image server 5 receives a request to register a medical image from the imaging apparatus 2, the image server 5 prepares the medical image in a format for a database and registers the medical image in the image database 6.

Image data of the medical image acquired by the imaging apparatus 2 and accessory information attached to the image data are registered in the image database 6. The accessory information includes, for example, an image identification (ID) for identifying each medical image, a patient ID for identifying a patient who is a subject, an examination ID for identifying an examination content, a unique ID (UID: unique identification) allocated for each medical image, examination date and examination time at which a medical image is generated, the type of imaging apparatus used in an examination for acquiring a medical image, patient information such as the name, age, and gender of a patient, an examination part (imaging part), imaging information (an imaging protocol, an imaging sequence, an imaging method, imaging conditions, the presence or absence of the use of a contrast medium, and the like), and information such as a series number or a collection number when a plurality of medical images are acquired in one examination. In addition, in a case where a viewing request from the interpretation WS 3 is received through the network 9, the image server 5 searches for a medical image registered in the image database 6 and transmits the searched for medical image to the interpretation WS 3 that is a request source.

The interpretation report server 7 incorporates a software program for providing a function of a database management system to a general-purpose computer. In a case where the interpretation report server 7 receives a request to register an interpretation report from the interpretation WS 3, the interpretation report server 7 prepares the interpretation report in a format for a database and registers the interpretation report in the interpretation report database 8. Further, in a case where the request to search for the interpretation report is received, the interpretation report is searched for from the interpretation report database 8.

In the interpretation report database 8, for example, an interpretation report is registered in which information, such as an image ID for identifying a medical image to be interpreted, a radiologist ID for identifying an image diagnostician who performed the interpretation, a lesion name, position information of a lesion, findings, and confidence of the findings, is recorded.

The network 9 is a wired or wireless local area network that connects various apparatuses in a hospital to each other. In a case where the interpretation WS 3 is installed in another hospital or clinic, the network 9 may be configured to connect local area networks of respective hospitals through the Internet or a dedicated line. In any case, it is preferable that the network 9 has a configuration capable of realizing high-speed transmission of medical images such as an optical network.

In the interpretation WS 3, each process such as requesting to view a medical image from the image server 5, various kinds of image processing on the medical image received from the image server 5, displaying the medical image, an analysis process on the medical image, highlighting the medical image based on the analysis result, creating the interpretation report based on the analysis result, supporting the creation of an interpretation report, requesting to register and view the interpretation report from the interpretation report server 7, and displaying the interpretation report received from the interpretation report server 7 is performed by executing a software program for each process. The interpretation WS 3 encompasses a document creation support apparatus 10 to be described later, and in the above processes, processes other than those performed by the document creation support apparatus 10 are performed by a well-known software program, and therefore the detailed description thereof will be omitted here. In addition, processes other than the processes performed by the document creation support apparatus 10 may not be performed in the interpretation WS 3, and a computer that performs the processes may be separately connected to the network 9, and in response to a processing request from the interpretation WS 3, the requested process may be performed by the computer. Hereinafter, the document creation support apparatus 10 encompassed in the interpretation WS 3 will be described in detail.

Figure 2:
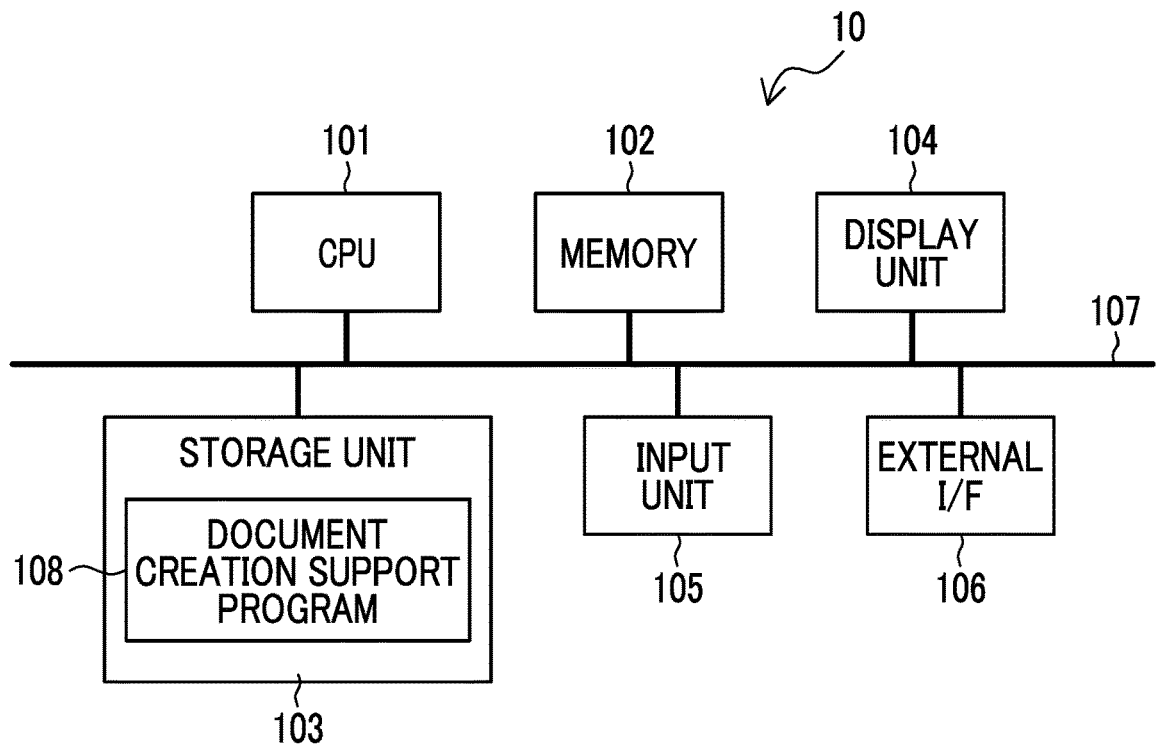
FIG. 2 is a diagram showing an example of a hardware configuration of a document creation support apparatus according to an embodiment of the disclosed technology.

FIG. 2 is a diagram showing an example of the hardware configuration of the document creation support apparatus 10. The document creation support apparatus 10 includes a central processing unit (CPU) 101, a memory 102, a storage unit 103, a display unit 104 such as a liquid crystal display, an input unit 105 such as a keyboard and a mouse, and an external interface (I/F) 106. The input unit 105 may be provided with a microphone that receives voice input. The CPU 101, the memory 102, the storage unit 103, the display unit 104, the input unit 105, and the external I/F 106 are connected to a bus 107. The document creation support apparatus 10 is connected to the network 9 of the medical information system 1 via the external I/F 106. The CPU 101 is an example of a processor in the disclosed technology.

The storage unit 103 is realized by a hard disk drive (HDD), a solid state drive (SSD), a flash memory, or the like. A document creation support program 108 is stored in the storage unit 103. The document creation support program 108 is recorded on a recording medium, such as a DVD or a CD-ROM, and distributed, and is installed on the document creation support apparatus 10 from the recording medium. Alternatively, the document creation support program is stored in a storage apparatus of a server computer connected to the network or in a network storage in a state in which it can be accessed from the outside, and is downloaded to and installed on the document creation support apparatus 10 in response to a request. The CPU 101 reads the document creation support program 108 from the storage unit 103, loads the read document creation support program 108 into the memory 102, and executes the loaded document creation support program 108.

Figure 3:
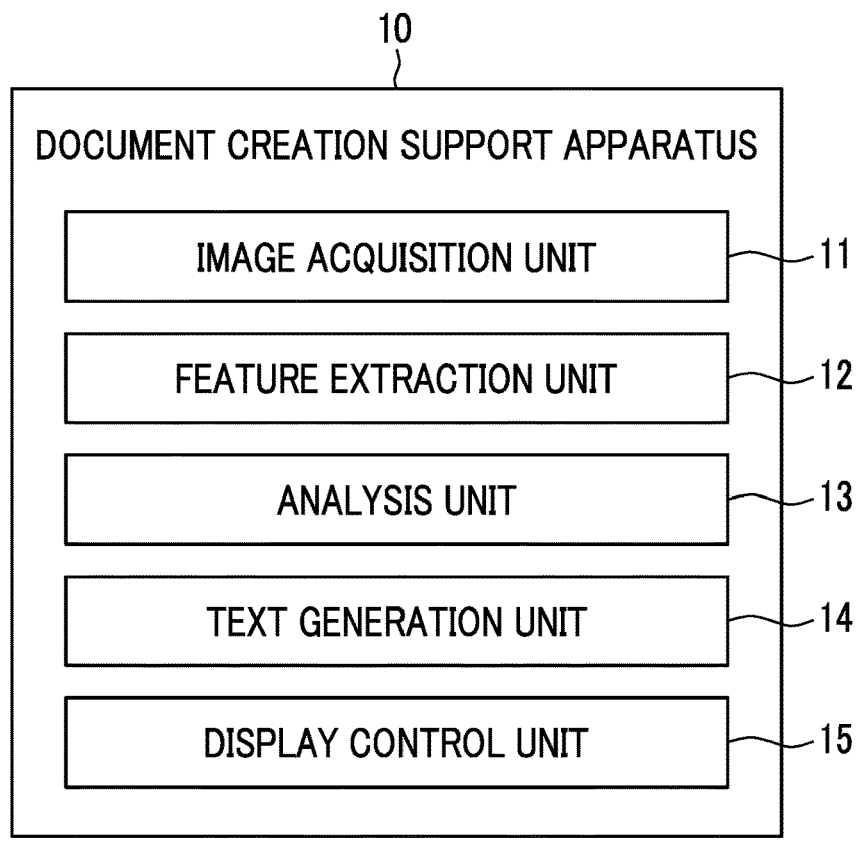
FIG. 3 is a functional block diagram showing an example of a functional configuration of the document creation support apparatus according to an embodiment of the disclosed technology.

FIG. 3 is a functional block diagram showing an example of the functional configuration of the document creation support apparatus 10. The document creation support apparatus 10 includes an image acquisition unit 11, a feature extraction unit 12, an analysis unit 13, a text generation unit 14, and a display control unit 15. The CPU 101 executes the document creation support program 108, so that the document creation support apparatus 10 functions as the image acquisition unit 11, the feature extraction unit 12, the analysis unit 13, the text generation unit 14, and the display control unit 15.

The image acquisition unit 11 acquires a medical image to be diagnosed (hereinafter referred to as a diagnosis target image). The diagnosis target image is saved in the image database 6, is transmitted from the image database 6 to the document creation support apparatus 10 in response to a request from the document creation support apparatus 10 (interpretation workstation 3), and is saved in the storage unit 103. The image acquisition unit 11 acquires the diagnosis target image saved in the storage unit 103. The image acquisition unit 11 may directly acquire the diagnosis target image saved in the image database 6 from the image database 6. In the following, a case where the diagnosis target image is a chest CT image will be described as an example.

Figure 4:
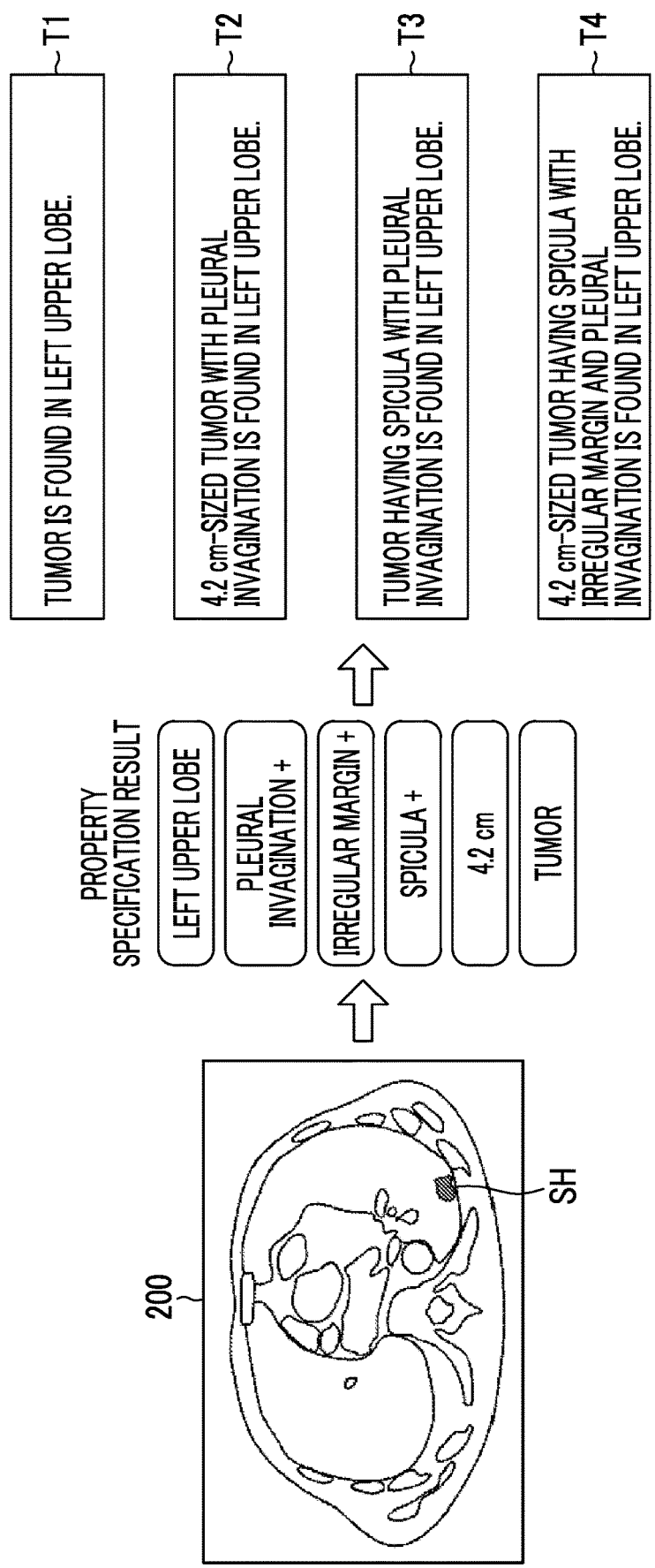
FIG. 4 is a diagram for describing a function of the document creation support apparatus according to an embodiment of the disclosed technology.

The feature extraction unit 12 extracts a shadow where a disease such as a nodule or tumor is suspected (hereinafter referred to as an abnormal shadow) as a feature portion from the diagnosis target image acquired by the image acquisition unit 11. The feature extraction unit 12 may extract an abnormal shadow using, for example, a trained model trained by machine learning such as deep learning. The above-mentioned trained model is trained by machine learning using, for example, a plurality of combinations of a medical image including an abnormal shadow and information specifying a region in the image in which the abnormal shadow is present as training data. The above-mentioned trained model uses a medical image as an input and outputs a result of specifying an abnormal shadow region in the medical image. FIG. 4 shows an example in which an abnormal shadow SH is extracted from a diagnosis target image 200.

The analysis unit 13 analyzes the abnormal shadow extracted by the feature extraction unit 12 to specify the properties of the abnormal shadow for each of a plurality of predetermined property items. Examples of the property items specified for the abnormal shadow include the position, the size, the presence or absence of spicula, the presence or absence of an irregular margin, the presence or absence of pleural invagination, and the type of disease in the corresponding abnormal shadow.

The analysis unit 13 may specify the property of an abnormal shadow using, for example, a trained model trained by machine learning such as deep learning. The above-mentioned trained model is trained by machine learning using, for example, a plurality of combinations of a medical image including an abnormal shadow and a property label representing the property of the abnormal shadow as training data. The above-mentioned trained model uses a medical image as an input, and outputs a property score derived for each property item in the abnormal shadow included in the medical image. The property score is a score indicating the prominence of the property for the property item. The property score takes a value of 0 or more and 1 or less, for example, and the larger the value of the property score is, the more pronounced the property is.

For example, in a case where the property score for "the presence or absence of spicula", which is one of the property items of an abnormal shadow, is, for example, 0.5 or more, the analysis unit 13 specifies that the property for "the presence or absence of spicula" of the corresponding abnormal shadow is "with spicula (positive)", and in a case where the property score for "the presence or absence of spicula" is less than, for example, 0.5, the analysis unit 13 specifies that the property for the presence or absence of spicula of the corresponding abnormal shadow is "no spicula (negative)". The threshold value 0.5 used for property determination is merely an example, and is set to an appropriate value for each property item.

FIG. 4 shows an example in which "left upper lobe", "pleural invagination+", "irregular margin+", "spicula+", "4.2 cm", and "tumor" are specified as the properties of each property item of the abnormal shadow SH extracted from a diagnosis target image 200. The "+" notation in the specified property indicates that the property is positive.

The text generation unit 14 generates, as candidate texts, a plurality of different texts describing the properties of the abnormal shadow for the abnormal shadows extracted by the feature extraction unit 12. The text generation unit 14 generates a plurality of texts such that at least one of the properties for each of a plurality of property items specified by the analysis unit 13 is described in each text. The text generation unit 14 generates the plurality of texts such that a combination of property items corresponding to the properties described in each of the plurality of texts is different between the plurality of texts.

FIG. 4 shows an example in which the text generation unit 14 generates four different texts describing the properties of the abnormal shadow SH. The text generation unit 14 generates a first text T1 including a description "A tumor is found in the left upper lobe" based on, for example, "left upper lobe" and "tumor" among the properties specified for each of the plurality of property items. Further, the text generation unit 14 generates a second text T2 including a description "A 4.2 cm-sized tumor with pleural invagination is found in the left upper lobe" based on, for example, "left upper lobe", "pleural invagination+", "4.2 cm", and "tumor" among the properties specified for each of the plurality of property items. Further, the text generation unit 14 generates a third text T3 including a description "A tumor having spicula with pleural invagination is found in the left upper lobe" based on, for example, "left upper lobe", "pleural invagination+", "spicula+", and "tumor" among the properties specified for each of the plurality of property items. Further, the text generation unit 14 generates a fourth text T4 including a description "A 4.2 cm-sized tumor having spicula with an irregular margin and pleural invagination is found in the left upper lobe" based on, for example, "left upper lobe", "pleural invagination+", "irregular margin+", "spicula+", "4.2 cm", and "tumor" among the properties specified for each of the plurality of property items.

In this way, the text generation unit 14 generates the plurality of texts such that at least one of the properties specified for each of a plurality of predetermined property items is described in each of the plurality of texts and a combination of property items corresponding to the properties described in each of the plurality of texts is different between the plurality of texts. The number of texts generated by the text generation unit 14 may be 3 or less, or 5 or more. In addition, the text generation unit 14 may generate texts for all combinations in which M (M<N) or more property items are selected from among the N property items. Further, the number of property items included in each text may be different from each other or may be the same among a plurality of texts. In addition, the user may designate essential property items to be included in each of the plurality of texts. In this case, the text generation unit 14 may generate a plurality of texts including the description regarding the essential property items and having different combinations of property items other than the essential property items.

Figure 5:
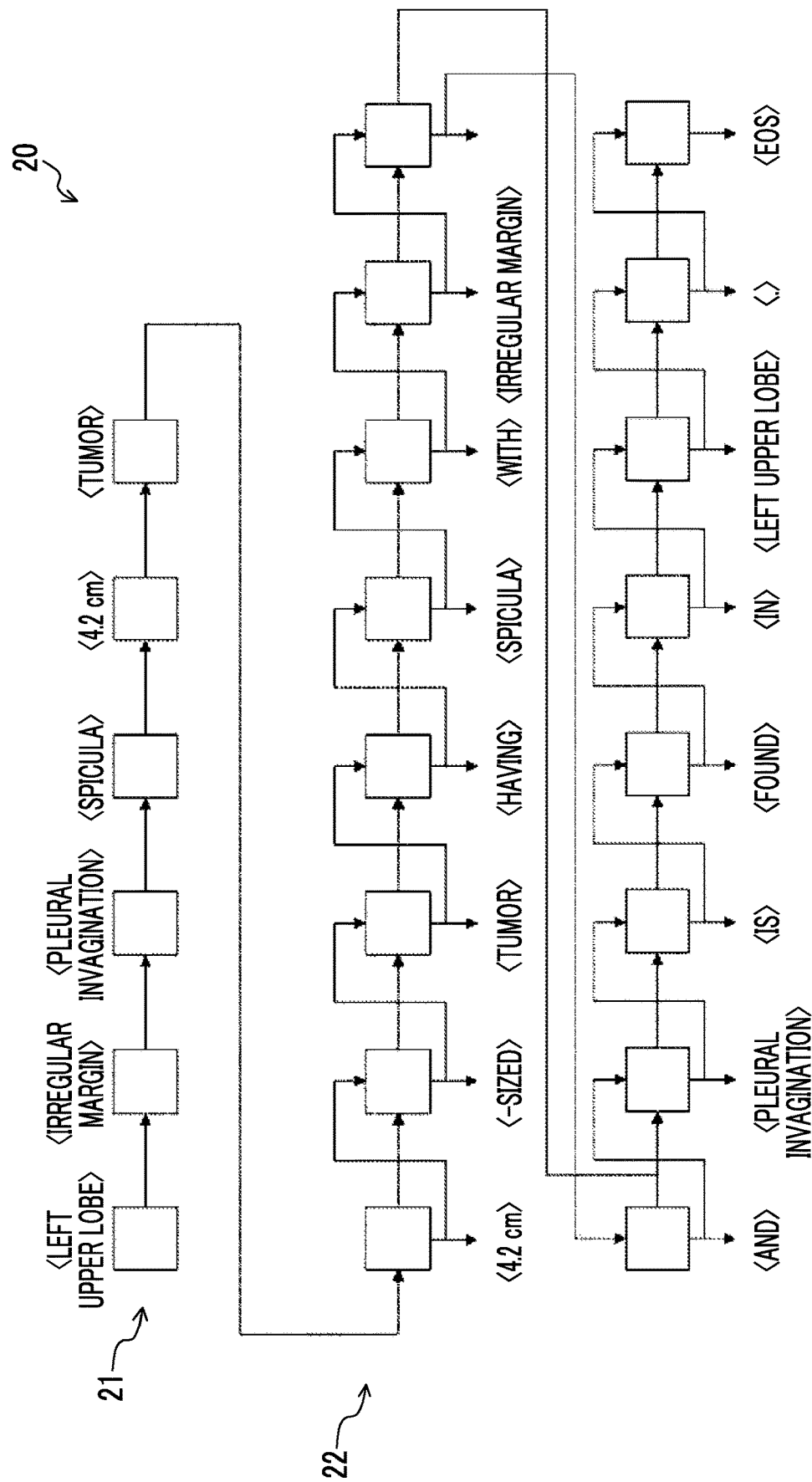
FIG. 5 is a diagram schematically showing an example of a configuration of a recurrent neural network constituting a text generation unit according to an embodiment of the disclosed technology.

The text generation unit 14 includes a recurrent neural network trained to create a text from input words. FIG. 5 is a diagram schematically showing a configuration of a recurrent neural network. As shown in FIG. 5, a recurrent neural network 20 includes an encoder 21 and a decoder 22. Characters corresponding to the property specified by the analysis unit 13 are input to the encoder 21. For example, in a case where the text generation unit 14 generates the fourth text T4 illustrated in FIG. 4, "left upper lobe", "pleural invagination", "irregular margin", "spicula", "4.2 cm", and "tumor", which are characters of the properties specified by the analysis unit 13, are input to the encoder 21. The decoder 22 has been trained to document the words input to the encoder 21, and from the above input words, the fourth text T4, "A 4.2 cm-sized tumor having spicula with an irregular margin and pleural invagination is found in the left upper lobe", is generated. In FIG. 5, "EOS" indicates the end of the sentence (End Of Sentence).

Figure 6:
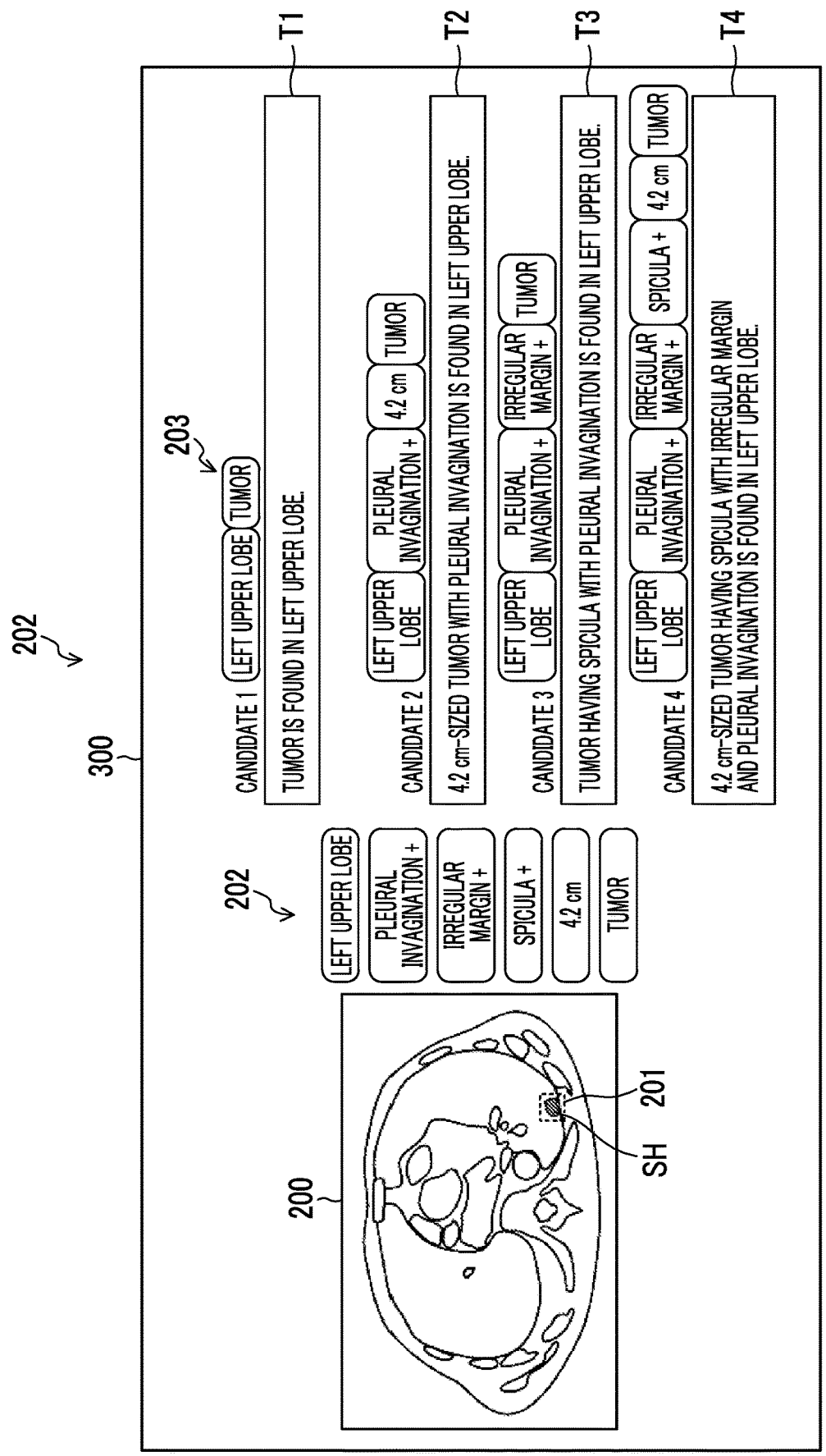
FIG. 6 is a diagram showing an example of a display mode of information displayed on a display screen according to an embodiment of the disclosed technology.

The display control unit 15 performs control such that the plurality of texts generated by the text generation unit 14 are displayed on the display unit 104. FIG. 6 is a diagram showing an example of a display mode of information displayed on a display screen 300 of the display unit 104 under the control of the display control unit 15. As shown in FIG. 6, the first to fourth texts T1 to T4 generated by the text generation unit 14 are displayed on the display screen 300. In addition, the diagnosis target image 200 including the abnormal shadow SH corresponding to the first to fourth texts T1 to T4 is displayed on the display screen 300. The diagnosis target image 200 may be provided with a mark 201 indicating the position of the abnormal shadow SH. In addition, on the display screen 300, a property label 202 indicating the properties of each property item specified for the abnormal shadow SH is displayed. Further, in the vicinity of each of the first to fourth texts T1 to T4, a property label 203 indicating the property described in the text is displayed. The user can select any one of the plurality of texts displayed on the display screen 300 and use the selected text as a part or all of the document (interpretation report) created by the user. The text can be selected, for example, by clicking the display region of the text to be selected with a pointer.

In the following, the operation of the document creation support apparatus 10 will be described. FIG. 7 is a flowchart showing an example of a flow of a document creation support process performed by the CPU 101 executing the document creation support program 108. The document creation support program 108 is executed, for example, in a case where an instruction to start execution is input by a user via the input unit 105. It is assumed that the diagnosis target image is downloaded from the image server 5 to the document creation support apparatus 10 (interpretation workstation 3) and is saved in the storage unit 103.

In Step ST1, the image acquisition unit 11 acquires the diagnosis target image saved in the storage unit 103. In Step ST2, the feature extraction unit 12 extracts abnormal shadows as feature portions from the diagnosis target image acquired by the image acquisition unit 11. In Step ST3, the analysis unit 13 analyzes the abnormal shadows extracted from the diagnosis target image, and specifies the properties of the abnormal shadow for each of the plurality of predetermined property items.

In Step ST4, the text generation unit 14 generates a plurality of different texts describing the properties specified in Step ST3. In this way, the text generation unit 14 generates the plurality of texts such that at least one of the properties for each of a plurality of predetermined property items is described in each of the plurality of texts and a combination of property items corresponding to the properties described in each of the plurality of texts is different between the plurality of texts.

In Step ST5, the display control unit 15 performs control such that the plurality of texts generated by the text generation unit 14 are displayed on the display screen of the display unit 104. The user can select any one of the plurality of texts displayed on the display unit 104 and use the selected text as a part or all of the document (interpretation report) created by the user.

As described above, with the document creation support apparatus 10 according to the embodiment of the disclosed technology, a plurality of different texts describing the properties of the abnormal shadow extracted from the diagnosis target image are generated as candidate documents. In a plurality of texts, a combination of property items corresponding to the properties described in each text is different from each other. Accordingly, it is possible to create a plurality of texts having a variety of description contents. As a result, there is a high likelihood that texts that match the user's request are included in the plurality of texts, and it is possible to effectively support the creation of a document (interpretation report) by the user.

Second Embodiment

FIG. 8 is a diagram showing an example of the property score derived by the analysis unit 13. As described above, the analysis unit 13 analyzes the abnormal shadow extracted by the feature extraction unit 12 to derive a property score indicating the prominence of the property for each property item for the corresponding abnormal shadow. In the present embodiment, the property score takes a value of 0 or more and 1 or less. The larger the property score is, the more pronounced the property is. The range of the property score is not limited to 0 or more and 1 or less, and can be appropriately determined.

Similarly to the first embodiment, the text generation unit 14 generates the plurality of texts such that a combination of property items described in each of the plurality of texts is different between the plurality of texts. In the present embodiment, the text generation unit 14 determines a combination of property items described in each of the plurality of texts based on the property score derived by the analysis unit 13. For example, the text generation unit 14 generates a text describing only properties having a property score of, for example, 0.9 or more as a first text, generates a text describing only properties having a property score of, for example, 0.7 or more as a second text, and generates a text describing only properties having a property score of, for example, 0.5 or more as a third text. The threshold value of the property score is not limited to 0.9, 0.7, and 0.5 described above, and can be appropriately set.

For example, in a case where the property score as shown in FIG. 8 is derived, the text generation unit 14 generates a first text including a description "A tumor is found in the left upper lobe" based on the properties "left upper lobe" and "tumor" having a property score of 0.9 or more. Further, the text generation unit 14 generates a second text including a description "A 4.2 cm-sized tumor with pleural invagination is found in the left upper lobe" based on the properties "left upper lobe", "pleural invagination+", "4.2 cm", and "tumor" having a property score of 0.7 or more. Further, the text generation unit 14 generates a third text including a description "A 4.2 cm-sized tumor having spicula with an irregular margin and pleural invagination is found in the left upper lobe" based on the properties "left upper lobe", "irregular margin", "pleural invagination+", "spicula", "4.2 cm", and "tumor" having a property score of 0.5 or more.

With the document creation support apparatus according to the second embodiment of the disclosed technology, it is possible to create a plurality of texts having a variety of description contents as in the first embodiment. In addition, by determining the combination of the property items described in the text according to the property score, it is possible to generate a plurality of texts having a different probability of the description contents. For example, it is possible to generate a plurality of texts including a first text including a description regarding a high-probability property item, a second text including a description regarding a medium-probability property item, and a third text including a description regarding a low-probability property item.

Third Embodiment

The text generation unit 14 according to the first and second embodiments described above generates the plurality of texts such that a combination of property items described in each of the plurality of texts is different between the plurality of texts. The text generation unit 14 according to a third embodiment of the disclosed technology generates the plurality of texts such that each text includes a description of the same content with different expressions between the plurality of texts.

Figure 9:
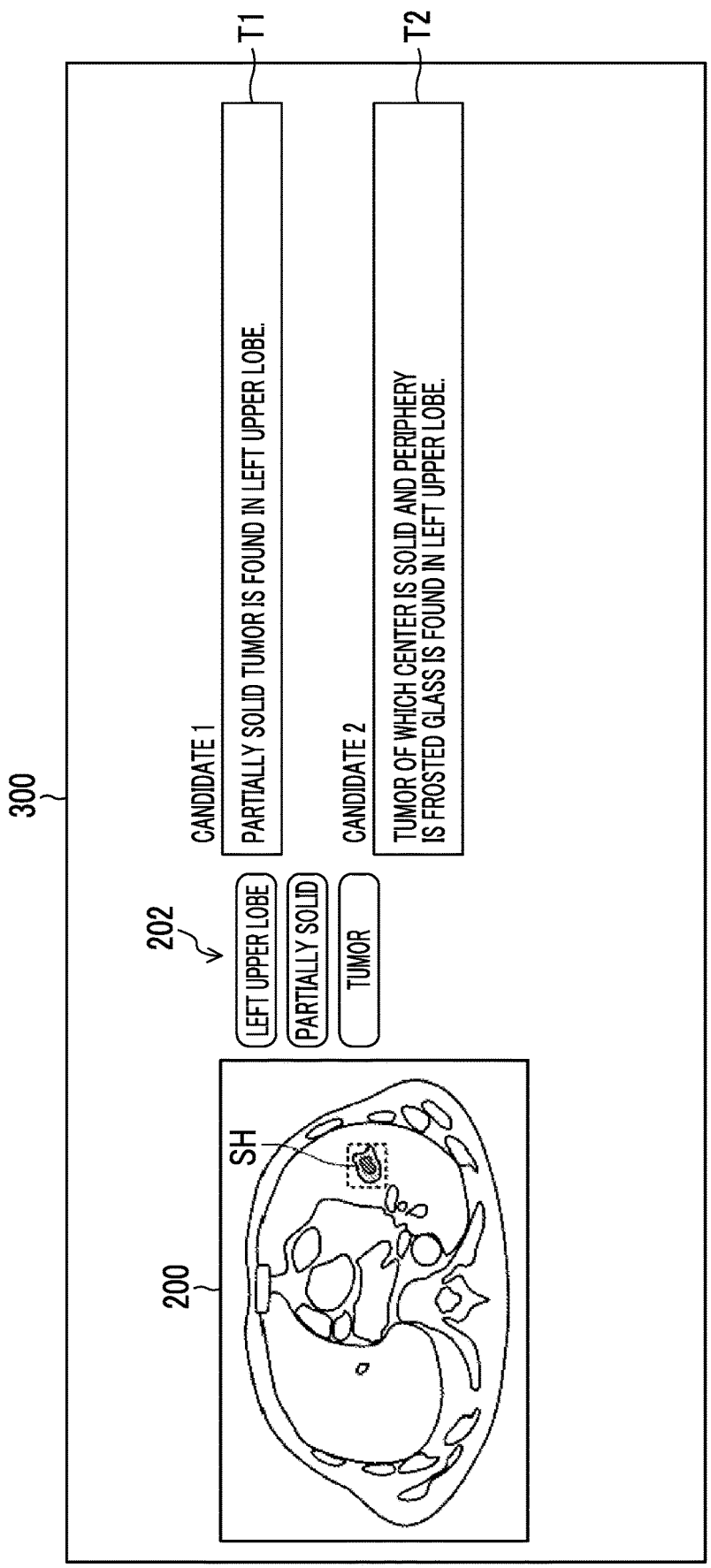
FIG. 9 is a diagram showing an example of a display mode of information displayed on the display screen according to an embodiment of the disclosed technology.

FIG. 9 is a diagram showing an example of a display mode of information displayed on the display screen 300 according to the third embodiment of the disclosed technology. FIG. 9 shows an example in which "left upper lobe", "partially solid", and "tumor" are specified by the analysis unit 13 as the properties of the abnormal shadow SH extracted from the diagnosis target image 200. On the display screen 300, the property label 202 indicating each of the above-mentioned properties specified for the abnormal shadow SH is displayed.

In this example, the text generation unit 14 generates a first text T1 including a description "A partially solid tumor is found in the left upper lobe" based on "left upper lobe", "partially solid", and "tumor", which are the properties specified for abnormal shadow SH. Further, the text generation unit 14 generates a second text T2 including a description "A tumor of which the center is solid and the periphery is frosted glass is found in the left upper lobe" based on "left upper lobe", "partially solid", and "tumor", which are the properties specified for abnormal shadow SH. Here, although the expressions of "partially solid" described in the first text T1 and "the center is solid and the periphery is frosted glass" described in the second text T2 are different, their meanings are the same. In this way, the text generation unit 14 according to the third embodiment of the disclosed technology generates the plurality of texts such that a description of the same content with different expressions between the plurality of texts is included. The text generation unit 14 according to the present embodiment can be realized by using a trained model trained to create a plurality of texts having the same content with different expressions from the input words.

With the document creation support apparatus according to the third embodiment of the disclosed technology, it is possible to create a plurality of texts having a variety of description contents as in the first embodiment. In addition, since a plurality of texts include descriptions of the same content with different expressions, there is a high likelihood that texts that match the user's request are included in the plurality of candidate texts, and it is possible to effectively support the creation of a document (interpretation report) by the user.

The text generation unit 14 may generate the plurality of texts such that a description of a designated property among a plurality of properties specified for the abnormal shadow has the same content with different expressions between the plurality of texts. By allowing the user to designate properties to be described in different expressions, it is possible to further increase the likelihood that text using expressions that match the user's request will be generated.

Fourth Embodiment

The document creation support apparatus according to the first to third embodiments described above generates a plurality of different texts describing the properties of the feature portions. The document creation support apparatus according to a fourth embodiment of the disclosed technology generates a plurality of different texts describing the classification of a disease corresponding to the feature portion. The same applies to the document creation support apparatus according to fifth to seventh embodiments to be described later. The classification of a disease includes, for example, disease names and diagnosis names such as nodules, hemangiomas, cysts, lymphadenopathy, pleural effusion, and hamartoma, and also includes the classification of whether the disease is benign or malignant (cancer).

In the present embodiment, the analysis unit 13 analyzes an abnormal shadow extracted from the diagnosis target image and estimates the classification of a disease corresponding to the abnormal shadow. The analysis unit 13 may estimate the classification of a disease using, for example, a trained model trained by machine learning such as deep learning. The above-mentioned trained model is trained by machine learning using, for example, training data in which a medical image including an abnormal shadow is given the classification of a disease corresponding to the abnormal shadow as a correct label. The analysis unit 13 derives a classification determination score indicating a probability that the disease corresponds to the classification for each candidate for the classification of the disease corresponding to the abnormal shadow.

The text generation unit 14 generates a plurality of different texts describing the classification of the disease corresponding to the abnormal shadow extracted from the diagnosis target image. More specifically, the text generation unit 14 generates the plurality of texts such that the classification of the disease described in each of the plurality of texts is different between the plurality of texts. For example, the text generation unit 14 may use all or some of the candidates for the classification of the disease for which a classification determination score is derived in the analysis unit 13 as the classification of the description target.

FIG. 10 shows an example in which the text generation unit 14 generates three texts describing the classifications of different diseases corresponding to the abnormal shadows extracted from the diagnosis target image. The text generation unit 14 generates a first text T1 including a description "A nodule is found" as a description regarding the classification of the disease corresponding to the abnormal shadow. In addition, the text generation unit 14 generates a second text T2 including a description "A hemangioma is found" as a description regarding the classification of the disease corresponding to the abnormal shadow. In addition, the text generation unit 14 generates a third text T3 including a description "A cyst is found" as a description regarding the classification of the disease corresponding to the abnormal shadow.

The display control unit 15 performs control such that the plurality of texts generated by the text generation unit 14 are arranged in order according to an estimation result of the classification of the disease in the analysis unit 13 and are displayed on the display unit 104. For example, in a case where the classification determination score of "nodule" is the highest among the classification determination scores derived for each candidate for the classification of the disease performed by the analysis unit 13, the display control unit 15 may dispose and display the first text T1 including the description "A nodule is found" on the upper portion on the display screen with respect to the other texts T2 and T3.

FIG. 11 is a diagram showing another example of a plurality of texts generated by the text generation unit 14. The text generation unit 14 generates a first text T1 including a description "Primary lung cancer is suspected" as a description regarding the classification of the disease corresponding to the abnormal shadow. In addition, the text generation unit 14 generates a second text T2 including a description "There is a high likelihood of benignity" as a description regarding the classification of the disease corresponding to the abnormal shadow. In this way, the classification of the disease may be the classification of whether the disease is benign or malignant, and the text generation unit 14 may generate both a text including a description that the disease is malignant and a text including a description that the disease is benign. Further, as illustrated in FIG. 11, each of the plurality of texts may include not only a description regarding the classification of the disease but also a description regarding the property of the abnormal shadow.

With the document creation support apparatus according to the fourth embodiment of the disclosed technology, since the classification of the disease is described in each of the plurality of texts, it is possible to effectively support the creation of a document (interpretation report) by the user. In addition, since a plurality of texts are generated such that the classification of the disease described in each text is different between the plurality of texts, it is possible to increase the likelihood that texts that match the user's request are included in the plurality of texts. Further, the display control unit 15 performs control such that the plurality of texts generated by the text generation unit 14 are arranged in order according to an estimation result of the classification of the disease in the analysis unit 13 and are displayed on the display unit 104. Therefore, it is possible to facilitate the selection of the text by the user.

Fifth Embodiment

Similarly to the case of the fourth embodiment described above, the text generation unit 14 according to a fifth embodiment of the disclosed technology generates a plurality of different texts describing the classification of the disease corresponding to the abnormal shadow extracted from the diagnosis target image. In the present embodiment, the text generation unit 14 generates the plurality of texts such that, in the description regarding the classification of the disease, an expression indicating a probability that the disease corresponds to the classification is different between the plurality of texts.

FIG. 12 shows an example in which the text generation unit 14 generates, for the classification of a disease (primary lung cancer), three texts having different expressions indicating a probability that the disease corresponds to the classification. The text generation unit 14 generates a first text T1 including a description using an assertive expression such as "It is primary lung cancer" as a description regarding the classification of the disease. That is, the first text T1 includes an expression indicating that a probability that the disease corresponds to primary lung cancer is extremely high. In addition, the text generation unit 14 generates a second text T2 including a description using a speculative expression such as "Primary lung cancer is suspected" as a description regarding the classification of the disease. That is, the second text T2 includes an expression indicating that a probability that the disease corresponds to primary lung cancer is relatively high. In addition, the text generation unit 14 generates a third text T3 including a description using an expression that is neither positive nor negative, such as "The likelihood of primary lung cancer cannot be denied" as a description regarding the classification of the disease. That is, the third text T3 includes an expression indicating that a probability that the disease corresponds to primary lung cancer is relatively low. As illustrated in FIG. 12, each of the plurality of texts may include not only a description regarding the classification of the disease but also a description regarding the property of the abnormal shadow.

In the document creation support apparatus according to the present embodiment, the analysis unit 13 may analyze an abnormal shadow extracted from the diagnosis target image and estimate the classification of a disease corresponding to the abnormal shadow. That is, the analysis unit 13 may derive a classification determination score indicating a probability that the disease corresponds to the classification for each candidate for the classification of the disease corresponding to the abnormal shadow. In this case, the text generation unit 14 may generate a plurality of texts having different expressions as described above for the classification of the disease having the highest classification determination score derived by the analysis unit 13. In addition, the text generation unit 14 may generate a plurality of texts having different expressions as described above for each of the classifications of two or more diseases having relatively high scores derived by the analysis unit 13.

With the document creation support apparatus according to the fifth embodiment of the disclosed technology, since a plurality of texts include descriptions regarding classifications of diseases with different expressions indicating a probability corresponding to the classification, there is a high likelihood that texts that match the user's request are included in the plurality of candidate texts, and it is possible to effectively support the creation of a document (interpretation report) by the user.

Sixth Embodiment

Figures 13, 14:
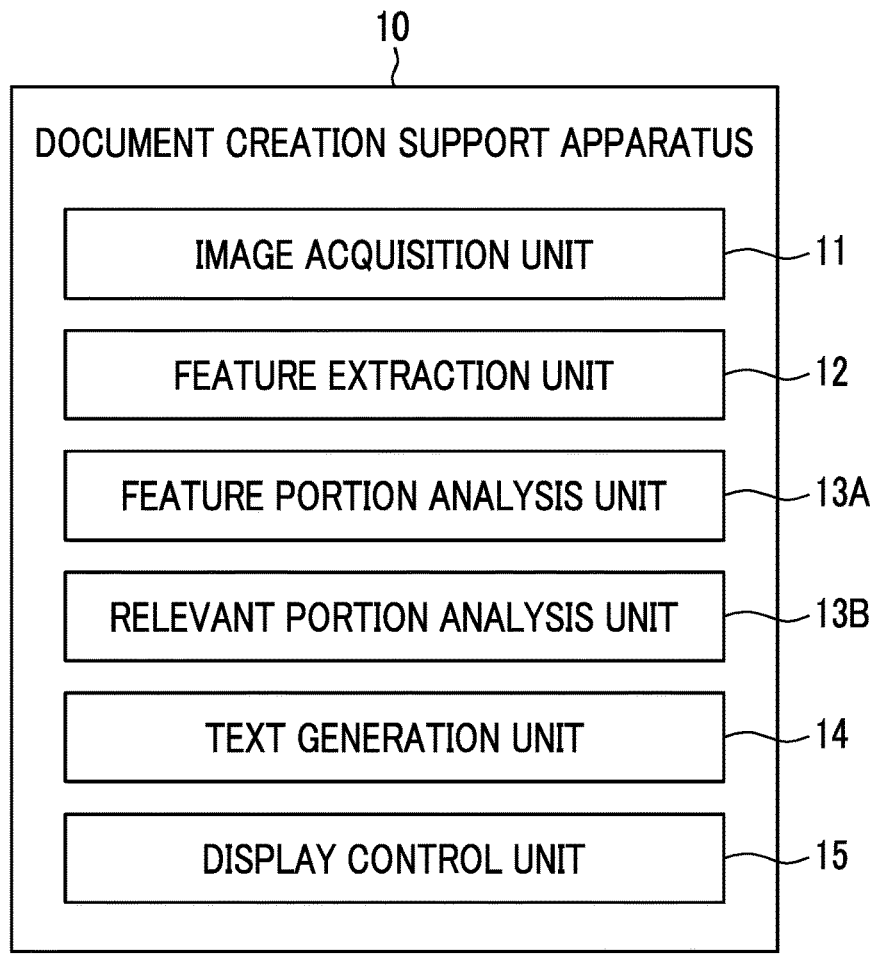
FIG. 13 is a functional block diagram showing an example of a functional configuration of the document creation support apparatus according to an embodiment of the disclosed technology.
FIG. 14 is a diagram showing an example of a table according to an embodiment of the disclosed technology.

FIG. 13 is a functional block diagram showing an example of a functional configuration of the document creation support apparatus according to a sixth embodiment of the disclosed technology. The document creation support apparatus 10 according to the present embodiment includes a feature portion analysis unit 13A and a relevant portion analysis unit 13B.

The feature portion analysis unit 13A analyzes an abnormal shadow extracted from the diagnosis target image and estimates the classification of a disease corresponding to the abnormal shadow. Specifically, the feature portion analysis unit 13A derives a classification determination score indicating a probability that the disease corresponds to the classification for each candidate for the classification of the disease corresponding to the abnormal shadow. That is, the function of the feature portion analysis unit 13A is the same as that of the analysis unit 13 according to the fourth embodiment described above.

The relevant portion analysis unit 13B specifies a relevant portion related to the classification of the disease having the highest classification determination score derived by the feature portion analysis unit 13A, and determines a predetermined determination item for the specified relevant portion. The relevant portion is a portion in the diagnosis target image in which the classification of other diseases that are expected to occur together with the classification of the disease corresponding to the abnormal shadow (feature portion) may occur.

FIG. 14 is an example of a table 30 referred to by the relevant portion analysis unit 13B. The table 30 is stored in the storage unit 103. For example, "lung nodule" is expected to occur together with "pleural effusion" and "lymphadenopathy". Therefore, in the table 30, the "lung nodule" is associated with "an area between the visceral pleura and the parietal pleura" where "pleural effusion" can occur as a first relevant portion, and is associated with the "lymph node" where "lymphadenopathy" can occur as a second relevant portion. Further, in the table 30, the "presence or absence of pleural effusion" is associated as a determination item for the first relevant portion, and the "presence or absence of lymphadenopathy" is associated as a determination item for the second relevant portion.

In a case where the classification of the disease having the highest classification determination score is "lung nodule", the relevant portion analysis unit 13B specifies "an area between the visceral pleura and the parietal pleura" as the first relevant portion based on the table 30, and determines the "presence or absence of pleural effusion" for the first relevant portion. Further, the relevant portion analysis unit 13B specifies the "lymph node" as the second relevant portion based on the table 30, and determines the "presence or absence of lymphadenopathy" for the second relevant portion.

Depending on the classification of the disease, there may be no relevant portion to be associated. For example, for "atelectasis", since there is no other disease that is expected to occur together with atelectasis, the field of the relevant portion associated with "atelectasis" in the table 30 is blank.

Similarly to the case of the fourth and fifth embodiments described above, the text generation unit 14 generates a plurality of different texts describing the classification of the disease corresponding to the abnormal shadow extracted from the diagnosis target image. In the present embodiment, the text generation unit 14 includes a description regarding the classification of the disease having the highest classification determination score derived by the feature portion analysis unit 13A in each of the plurality of texts. In addition, the text generation unit 14 includes, in each of the plurality of texts, a description regarding the relevant portion related to the classification of the disease corresponding to the abnormal shadow described in each of the plurality of texts. The text generation unit 14 generates a description regarding the relevant portion based on the determination result for the relevant portion derived by the relevant portion analysis unit 13B. In the present embodiment, the text generation unit 14 generates the plurality of texts such that the number or combination of relevant portions described in the plurality of texts is different between the plurality of texts.

FIG. 15 is a diagram showing an example of a plurality of texts generated by the text generation unit 14. Here, it is assumed that the classification of the disease having the highest classification determination score derived by the feature portion analysis unit 13A is "solid nodule". In response to this, it is assumed that the relevant portion analysis unit 13B specifies an area between the visceral pleura and the parietal pleura as a first relevant portion, and derives "no pleural effusion" as the determination result for the first relevant portion. Further, it is assumed that the relevant portion analysis unit 13B specifies a lymph node as a second relevant portion and derives "no lymphadenopathy" as the determination result for the second relevant portion.

The text generation unit 14 generates a first text T1 including a description "A solid nodule with a major axis of 2.1 cm is found in the left upper lobe. No pleural effusion is found." That is, the first text T1 includes "solid nodule" as a description regarding the classification of the disease corresponding to the abnormal shadow, and a description "No pleural effusion is found" as a description regarding the relevant portion.

In addition, the text generation unit 14 generates a second text T2 including a description "A solid nodule with a major axis of 2.1 cm is found in the left upper lobe. No lymphadenopathy is found." That is, the second text T2 includes a description "solid nodule" as a description regarding the classification of the disease corresponding to the abnormal shadow, and a description "No lymphadenopathy is found" as a description regarding the relevant portion.

In addition, the text generation unit 14 generates a third text T3 including a description "A solid nodule with a major axis of 2.1 cm is found in the left upper lobe. No pleural effusion is found. No lymphadenopathy is found." That is, the third text T3 includes a description "solid nodule" as a description regarding the classification of the disease corresponding to the abnormal shadow, and a description "No pleural effusion is found" and a description "No lymphadenopathy is found" as a description regarding the relevant portion. The text generation unit 14 may further generate a fourth text (not shown) that includes a description regarding the classification of the disease corresponding to the abnormal shadow and that does not include a description regarding the relevant portion.

The display control unit 15 performs control such that the plurality of texts generated by the text generation unit 14 are displayed on the display unit 104.

Figure 16:
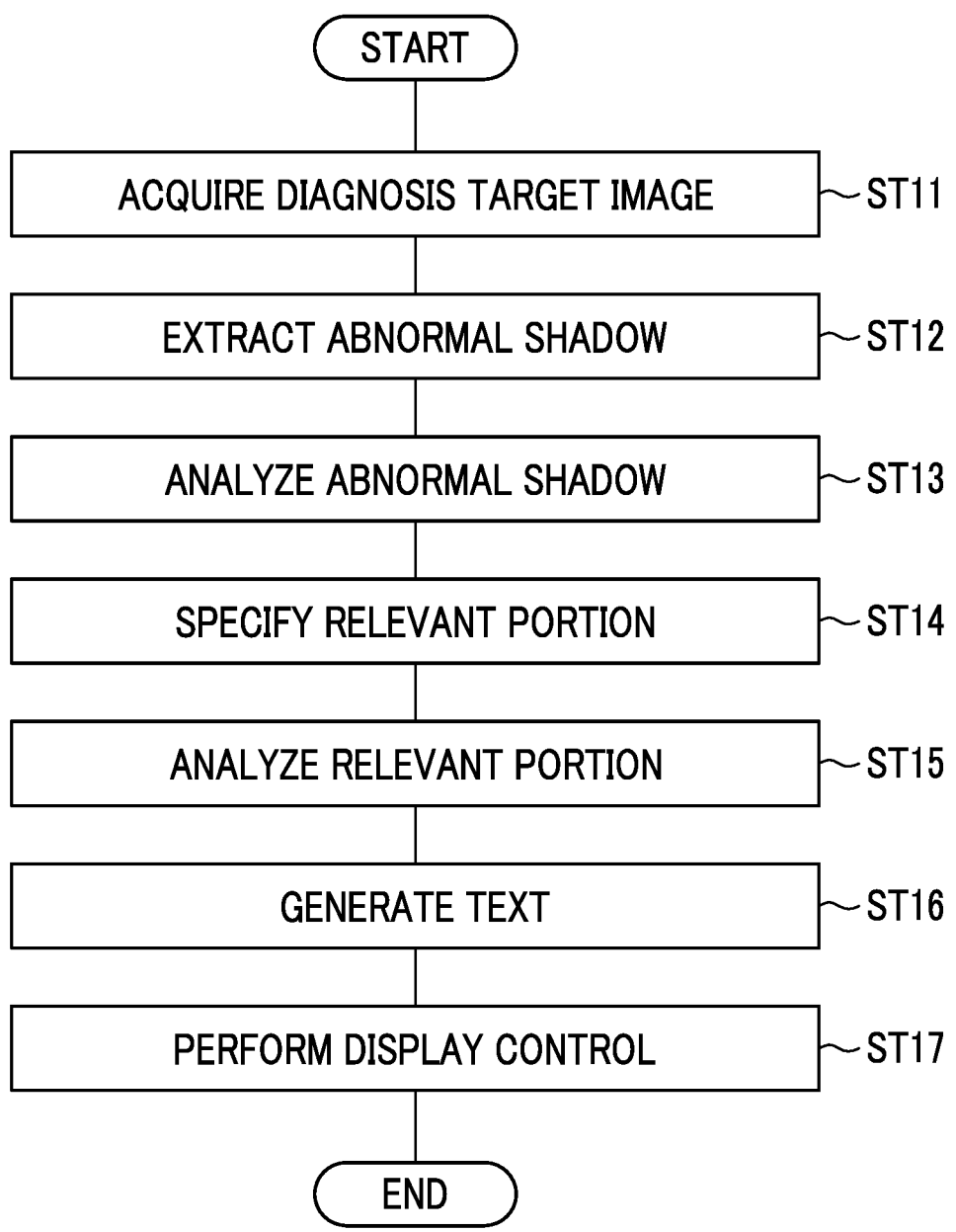
FIG. 16 is a flowchart showing an example of a flow of the document creation support process according to an embodiment of the disclosed technology.

Hereinafter, the operation of the document creation support apparatus according to the present embodiment will be described. FIG. 16 is a flowchart showing an example of a flow of a document creation support process performed by the CPU 101 executing the document creation support program 108 according to the present embodiment.

In Step ST11, the image acquisition unit 11 acquires the diagnosis target image saved in the storage unit 103. In Step ST12, the feature extraction unit 12 extracts abnormal shadows as feature portions from the diagnosis target image acquired by the image acquisition unit 11. In Step ST13, the feature portion analysis unit 13A analyzes the abnormal shadow extracted from the diagnosis target image, and derives a classification determination score indicating a probability that the disease corresponds to the classification for each candidate for the classification of the disease corresponding to the abnormal shadow.

In Step ST14, the relevant portion analysis unit 13B specifies the relevant portion related to the classification of the disease having the highest classification determination score derived by the feature portion analysis unit 13A in Step ST13 based on the table 30. In Step ST15, the relevant portion analysis unit 13B analyzes the relevant portion specified in Step ST14, and determines a predetermined determination item for the relevant portion. The relevant portion analysis unit 13B specifies a determination item based on the table 30.

In Step ST16, the text generation unit 14 generates a plurality of texts including a description regarding the classification of the disease having the highest classification determination score derived by the feature portion analysis unit 13A in Step ST13 and a description regarding the determination result for the relevant portion derived by the relevant portion analysis unit 13B in Step ST15.

In Step ST17, the display control unit 15 performs control such that the plurality of texts generated by the text generation unit 14 in Step ST16 are displayed on the display screen of the display unit 104. The user can select any one of the plurality of texts displayed on the display unit 104 and use the selected text as a part or all of the document (interpretation report) created by the user.

With the document creation support apparatus according to the sixth embodiment of the disclosed technology, since each of the plurality of texts includes not only a description regarding the classification of the disease corresponding to the abnormal shadow but also a description regarding the relevant portion related to the classification of the disease, it is possible to effectively support the creation of a document (interpretation report) by the user. In addition, since a plurality of texts are generated such that the number or combination of relevant portions described in each text is different between the plurality of texts, it is possible to increase the likelihood that texts that match the user's request are included in the plurality of texts.

In the present embodiment, a case in which the text generation unit 14 includes a description regarding the classification of the disease having the highest classification determination score derived by the feature portion analysis unit 13A in each of the plurality of texts has been exemplified, but the present disclosure is not limited to this aspect. Similarly to the case of the fourth embodiment described above, the text generation unit 14 may generate the plurality of texts such that the classification of the disease described in each of the plurality of texts is different between the plurality of texts. For example, the text generation unit 14 may use all or some of the candidates for the classification of the disease for which a classification determination score is derived in the feature portion analysis unit 13A as the classification of the description target. In this case, the relevant portion analysis unit 13B specifies the relevant portion for each classification of all or some of the candidates for the classification of the disease for which the classification determination score is derived, and determines a predetermined determination item for the specified relevant portion. The text generation unit 14 generates a description regarding the relevant portion corresponding to the classification of the disease described in each text based on the determination result for the relevant portion derived by the relevant portion analysis unit 13B, and includes the generated description in a corresponding text. As shown in the table 30 (see FIG. 14), in a case where there is no relevant portion related to the classification of the disease corresponding to the abnormal shadow, the text describing the classification of such a disease does not include the description regarding the relevant portion. That is, the text generation unit 14 includes a description regarding the relevant portion only in a text, among the plurality of texts, in which the classification of the disease described for the abnormal shadow is a specific classification.

FIG. 17 is a diagram showing another example of a plurality of texts that can be generated by the text generation unit 14. The text generation unit 14 generates a first text T1 including a description "A solid nodule with a major axis of 2.1 cm is found in the left upper lobe. No pleural effusion is found. No lymphadenopathy is found." That is, the first text T1 includes "solid nodule" as a description regarding the classification of the disease corresponding to the abnormal shadow, and a description "No pleural effusion is found" and a description "No lymphadenopathy is found" as a description regarding the relevant portion.

In addition, the text generation unit 14 generates a second text T2 including a description "Atelectasis with a major axis of 2.1 cm is found in the left upper lobe." That is, the second text T2 includes a description "atelectasis" as a description regarding the classification of the disease corresponding to the abnormal shadow, and does not include the description regarding the relevant portion. The reason why the second text T2 does not include the description regarding the relevant portion is that the relevant portion related to "atelectasis" is not present and the determination result for the relevant portion is not present.

FIG. 18 is a diagram showing another example of a plurality of texts generated by the text generation unit 14. The text generation unit 14 generates a first text T1 including a description "A solid nodule with a major axis of 2.1 cm is found in the left upper lobe. Primary lung cancer is suspected. No pleural effusion is found. No lymphadenopathy is found." That is, the first text T1 includes a description "solid nodule" and a description "Primary lung cancer is suspected" as a description regarding the classification of the disease corresponding to the abnormal shadow, and a description "No pleural effusion is found" and a description "No lymphadenopathy is found" as a description regarding the relevant portion. In addition, the text generation unit 14 generates a second text T2 including a description "A solid nodule with a major axis of 2.1 cm is found in the left upper lobe. There is a high likelihood of benignity." That is, the second text T2 includes a description "solid nodule" and a description "There is a high likelihood of benignity" as a description regarding the classification of the disease corresponding to the abnormal shadow, and does not include a description regarding the relevant portion.

In this way, the text generation unit 14 may include the description regarding the relevant portion in the text in which the classification of the disease described for the abnormal shadow is malignant among the plurality of texts, while the text generation unit 14 may not include the description regarding the relevant portion in the text in which the classification of the disease described for the abnormal shadow is benign. This is because for benign diseases, it is common that the relevant portion is not present, or even though the relevant portion is present, there is no interest in the relevant portion.

Seventh Embodiment

Figure 19:
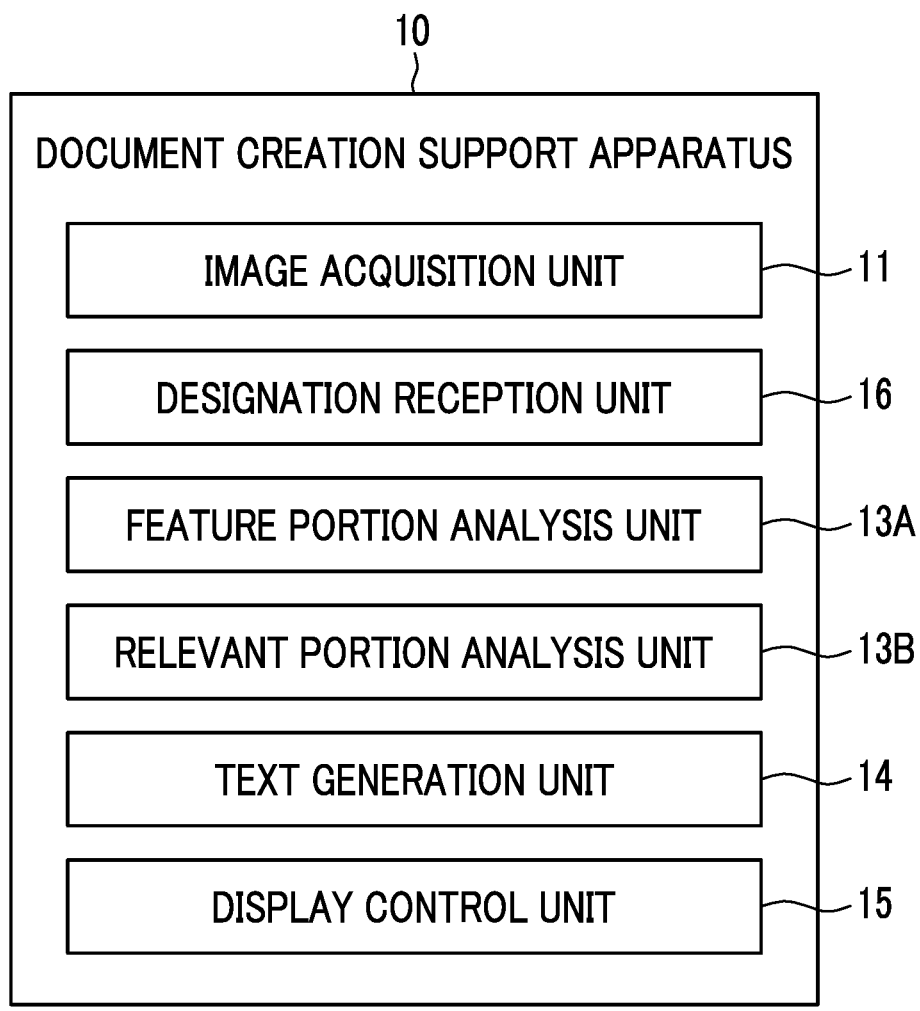
FIG. 19 is a functional block diagram showing an example of a functional configuration of the document creation support apparatus according to an embodiment of the disclosed technology.

FIG. 19 is a functional block diagram showing an example of a functional configuration of the document creation support apparatus according to a seventh embodiment of the disclosed technology. The document creation support apparatus 10 according to the present embodiment is different from the document creation support apparatus 10 (see FIG. 13) according to the sixth embodiment described above in that it includes a designation reception unit 16 instead of the feature extraction unit 12.

The designation reception unit 16 receives the designation of the abnormal shadow (feature portion) included in the diagnosis target image. The abnormal shadow can be designated, for example, by the user clicking or dragging a partial region in the diagnosis target image displayed on the display screen of the display unit 104 using an input device such as a mouse.

The feature portion analysis unit 13A analyzes an abnormal shadow according to the designation received by the designation reception unit 16 and estimates the classification of the disease corresponding to the abnormal shadow. Specifically, the feature portion analysis unit 13A derives a classification determination score indicating a probability that the disease corresponds to the classification for each candidate for the classification of the disease corresponding to the designated abnormal shadow.

The relevant portion analysis unit 13B specifies a relevant portion related to the classification of the disease having the highest classification determination score derived by the feature portion analysis unit 13A, and determines a predetermined determination item for the specified relevant portion.

The text generation unit 14 generates a plurality of different texts describing the classification of the disease corresponding to the abnormal shadow according to the designation received by the designation reception unit 16. In the present embodiment, the text generation unit 14 includes a description regarding the classification of the disease having the highest classification determination score derived by the feature portion analysis unit 13A in each of the plurality of texts. The text generation unit 14 includes, in each of the plurality of texts, a description regarding the relevant portion related to the classification of the disease corresponding to the abnormal shadow described in each of the plurality of texts. The text generation unit 14 generates a description regarding the relevant portion based on the determination result for the relevant portion derived by the relevant portion analysis unit 13B. The text generation unit 14 generates the plurality of texts such that the number or combination of relevant portions described in the plurality of texts is different between the plurality of texts. The display control unit 15 performs control such that the plurality of texts generated by the text generation unit 14 are displayed on the display unit 104.

With the document creation support apparatus according to the seventh embodiment of the disclosed technology, since the plurality of texts are generated for the abnormal shadow (feature portion) designated by the user, it is possible to effectively support the creation of a document (interpretation report) by the user.

In the present embodiment, a case in which the text generation unit 14 includes a description regarding the classification of the disease having the highest classification determination score derived by the feature portion analysis unit 13A in each of the plurality of texts has been exemplified, but the present disclosure is not limited to this aspect. Similarly to the case of the fourth embodiment described above, the text generation unit 14 may generate the plurality of texts such that the classification of the disease described in each of the plurality of texts is different between the plurality of texts. For example, the text generation unit 14 may use all or some of the candidates for the classification of the disease for which a classification determination score is derived in the feature portion analysis unit 13A as the classification of the description target. In this case, the relevant portion analysis unit 13B specifies the relevant portion for each classification of all or some of the candidates for the classification of the disease for which the classification determination score is derived, and determines a predetermined determination item for the specified relevant portion. The text generation unit 14 generates a description regarding the relevant portion corresponding to the classification of the disease described in each text based on the analysis result in the relevant portion analysis unit 13B, and includes the generated description in a corresponding text.

The document creation support apparatus may generate and display a plurality of texts as follows. For example, before receiving the designation of the abnormal shadow (feature portion) by the user, a plurality of texts may be generated in advance for each of the plurality of abnormal shadows (feature portions). After that, in a case where an abnormal shadow (feature portion) is designated by the user, control may be performed such that a plurality of texts related to the designated abnormal shadow (feature portion) are selected from among a plurality of texts generated in advance, and the selected plurality of texts are displayed on the display unit 104. The plurality of displayed texts may or may not include a description regarding the relevant portion.

Further, the description regarding the property of the abnormal shadow (feature portion) included in each of the plurality of texts may be a description regarding the size of the abnormal shadow (feature portion). That is, the text generation unit 14 may generate the plurality of texts such that a description regarding the size of the abnormal shadow (feature portion) is different between the plurality of texts. For example, the text generation unit 14 may generate a first text including a description "A cyst is found", a second text including a description "A small cyst is found", and a third text including a description "A microcyst is found."

Further, the description regarding the property of the abnormal shadow (feature portion) included in each of the plurality of texts may be a description regarding the number, an amount, a density, or a distribution state of the abnormal shadows (feature portions). That is, the text generation unit 14 may generate the plurality of texts such that a description regarding the number, an amount, a density, or a distribution state of the abnormal shadows (feature portions) is different between the plurality of texts. For example, the text generation unit 14 may generate a first text including a description "A cyst is found", a second text including a description "Cysts are scattered", and a third text including a description "Multiple cysts are found."

Further, as hardware structures of processing units that execute various kinds of processing such as each functional unit of the document creation support apparatus 10 according to the first to seventh embodiments described above, various processors shown below can be used. As described above, the various processors include a programmable logic device (PLD) as a processor of which the circuit configuration can be changed after manufacture, such as a field programmable gate array (FPGA), a dedicated electrical circuit as a processor having a dedicated circuit configuration for executing specific processing such as an application specific integrated circuit (ASIC), and the like, in addition to the CPU as a general-purpose processor that functions as various processing units by executing software (programs).

One processing unit may be configured by one of the various processors, or may be configured by a combination of the same or different kinds of two or more processors (for example, a combination of a plurality of FPGAs or a combination of the CPU and the FPGA). In addition, a plurality of processing units may be configured by one processor.

As an example where a plurality of processing units are configured by one processor, first, there is a form in which one processor is configured by a combination of one or more CPUs and software as typified by a computer, such as a client or a server, and this processor functions as a plurality of processing units. Second, there is a form in which a processor for realizing the function of the entire system including a plurality of processing units via one integrated circuit (IC) chip as typified by a system on chip (SoC) or the like is used. In this way, various processing units are configured by using one or more of the above-described various processors as hardware structures.

Furthermore, as the hardware structure of the various processors, more specifically, an electrical circuit (circuitry) in which circuit elements such as semiconductor elements are combined can be used.

The disclosures of Japanese Patent Application No. 2020-020144 filed on Feb. 7, 2020 and Japanese Patent Application No. 2020-212842 filed on Dec. 22, 2020 are incorporated herein by reference in their entirety. Further, all literatures, patent applications, and technical standards described herein are incorporated by reference to the same extent as if the individual literatures, patent applications, and technical standards were specifically and individually stated to be incorporated by reference.

What is claimed is:

1. A document creation support apparatus comprising at least one processor,
   wherein the processor is configured to
   receive a medical image,
   perform feature extraction on the medical image so as to extract at least one feature portion from the medical image,
   analyze the at least one feature portion to specify a plurality of properties of the at least one feature portion for each of a plurality of predetermined property items,
   derive a property score indicating a prominence of the property for each of the plurality of property items by using a trained model trained by machine learning, wherein a larger property score corresponds to a more pronounced property for each of the plurality of property items,
   generate a plurality of candidate texts including different descriptions for the at least one feature portion included in the medical image such that at least one of the specified properties is described in each of the plurality of candidate texts, wherein each of the plurality of candidate texts is respectively generated based on different ranges of property scores, and wherein a combination of property items corresponding to the properties described in each of the plurality of candidate texts is different, and
   perform control such that each of the plurality of candidate texts for selection and the medical image with the at least one feature portion being marked are displayed on a display.

2. The document creation support apparatus according to claim 1, wherein the processor is configured to generate the plurality of candidate texts such that each candidate text includes a description of the same content with different expressions.

3. The document creation support apparatus according to claim 2, wherein the processor is configured to generate the plurality of candidate texts such that a description of a designated property among the plurality of properties specified for the at least one feature portion in each of the plurality of texts has the same content with different expressions.

4. The document creation support apparatus according to claim 1, wherein each of the plurality of candidate texts is respectively generated further based on a classification of a disease corresponding to the at least one feature portion.

5. The document creation support apparatus according to claim 4, wherein the processor is configured to generate the plurality of candidate texts such that the classification of the disease described in each of the plurality of candidate texts is different.

6. The document creation support apparatus according to claim 5, wherein the processor is configured to
   estimate the classification of the disease corresponding to the at least one feature portion, and
   perform control such that the plurality of candidate texts are arranged in order according to an estimation result of the classification of the disease and are displayed on the display.

7. The document creation support apparatus according to claim 5, wherein the processor is configured to generate the plurality of candidate texts such that both a text indicating that the disease is benign and a text indicating that the disease is malignant are included.

8. The document creation support apparatus according to claim 4, wherein the processor is configured to generate the plurality of candidate texts such that, in the description regarding the classification of the disease, an expression indicating a probability that the disease corresponds to the classification in each of the plurality of candidate texts is different.

9. The document creation support apparatus according to claim 4, wherein the processor includes, in at least one of the plurality of candidate texts, a description regarding a relevant portion related to the classification of the disease described in each of the plurality of candidate texts for the at least one feature portion.

10. The document creation support apparatus according to claim 9, wherein the processor is configured to generate the plurality of candidate texts such that the number or combination of the relevant portions described in each of the plurality of candidate texts is different.

11. The document creation support apparatus according to claim 9, wherein the processor includes the description regarding the relevant portion only in a text, among the plurality of candidate texts, in which the classification of the disease described for the at least one feature portion is a specific classification.

12. The document creation support apparatus according to claim 11, wherein the processor includes the description regarding the relevant portion only in a text, among the plurality of candidate texts, in which the classification of the disease described for the at least one feature portion is malignant.

13. The document creation support apparatus according to claim 1, wherein the processor is configured to receive a designation of the at least one feature portion, and includes, in at least one of the plurality of candidate texts, a description regarding a relevant portion related to a classification of a disease corresponding to the designated feature portion.

14. The document creation support apparatus according to claim 1, wherein the processor is configured to
receive a designation of the at least one feature portion, and
perform control such that a plurality of candidate texts related to the designated feature portion among a plurality of texts generated in advance are displayed on the display.

15. The document creation support apparatus according to claim 1, wherein the processor is configured to generate the plurality of candidate texts such that a description regarding a size of the at least one feature portion in each of the plurality of candidate texts is different.

16. The document creation support apparatus according to claim 1, wherein the processor is configured to generate the plurality of candidate texts such that a description regarding the number, an amount, a density, or a distribution state of the at least one feature portion in each of the plurality of candidate texts is different.

17. The document creation support apparatus according to claim 1, wherein the at least one feature portion is an abnormal shadow where a disease is suspected.

18. The document creation support apparatus according to claim 1,
wherein the plurality of candidate texts comprise a first candidate text and a second candidate text,
wherein property scores of property items corresponding to properties described in the first candidate text are above a first threshold value, and
wherein property scores of property items corresponding to properties described in the second candidate text are above a second threshold value lower than the first threshold value.

19. A document creation support method comprising:
receiving a medical image;
performing feature extraction on the medical image so as to extract at least one feature portion from the medical image;
analyzing the at least one feature portion to specify a plurality of properties of the at least one feature portion for each of a plurality of predetermined property items;
deriving a property score indicating a prominence of the property for each of the plurality of property items by using a trained model trained by machine learning, wherein a larger property score corresponds to a more pronounced property for each of the plurality of property items;
generating a plurality of candidate texts including different descriptions for the at least one feature portion included in the medical image such that at least one of the specified properties is described in each of the plurality of candidate texts, wherein each of the plurality of candidate texts is respectively generated based on different ranges of property scores, and wherein a combination of property items corresponding to the properties described in each of the plurality of candidate texts is different; and
displaying each of the plurality of candidate texts for selection and the medical image with the at least one feature portion being marked on a display.

20. A non-transitory computer-readable storage medium storing a program for causing a computer to execute a process comprising:
deriving a property score indicating a prominence of the property for each of the receiving a medical image;
performing feature extraction on the medical image so as to extract at least one feature portion from the medical image;
analyzing the at least one feature portion to specify a plurality of properties of the at least one feature portion for each of a plurality of predetermined property items;
deriving a property score indicating a prominence of the property for each of the plurality of property items by using a trained model trained by machine learning, wherein a larger property score corresponds to a more pronounced property for each of the plurality of property items;
generating a plurality of candidate texts including different descriptions for the at least one feature portion included in the medical image such that at least one of the specified properties is described in each of the plurality of candidate texts, wherein each of the plurality of candidate texts is respectively generated based on different ranges of property scores, and wherein a combination of property items corresponding to the properties described in each of the plurality of candidate texts is different; and
displaying each of the plurality of candidate texts for selection and the medical image with the at least one feature portion being marked on a display.

* * * * *